(12) United States Patent
Bonnet

(10) Patent No.: US 7,294,747 B2
(45) Date of Patent: Nov. 13, 2007

(54) METHOD OF PRODUCING 1,1-DIFLUOROETHANE AND APPLICATION THEREOF FOR THE PRODUCTION OF 1,1-DIFLUOROETHYLENE

(75) Inventor: Phillipe Bonnet, Lyons (FR)

(73) Assignee: Arkema France, Colombes (FR)

( * ) Notice: Subject to any disclaimer, the term of this patent is extended or adjusted under 35 U.S.C. 154(b) by 104 days.

(21) Appl. No.: 10/573,125

(22) PCT Filed: Oct. 17, 2003

(86) PCT No.: PCT/FR03/03074

§ 371 (c)(1),
(2), (4) Date: Mar. 23, 2006

(87) PCT Pub. No.: WO2005/047219

PCT Pub. Date: May 26, 2005

(65) Prior Publication Data

US 2007/0066857 A1   Mar. 22, 2007

(51) Int. Cl.
*C07C 17/20* (2006.01)

(52) U.S. Cl. .................. 570/160; 570/165; 570/168
(58) Field of Classification Search .............. None
See application file for complete search history.

(56) References Cited

U.S. PATENT DOCUMENTS

| 2,452,975 A | 11/1948 | Whalley et al. ............ 260/653 |
| 4,148,831 A | 4/1979 | Schultz et al. ........... 260/653.5 |
| 5,545,775 A | 8/1996 | Thenappan et al. ......... 570/168 |
| 5,672,788 A | 9/1997 | Nappa et al. ............... 570/168 |
| 5,714,650 A | 2/1998 | Wuttke ....................... 570/165 |

FOREIGN PATENT DOCUMENTS

| FR | 2 842 802 | 1/2004 |
| JP | 50 106904 | 2/1974 |
| JP | 50 106905 | 2/1974 |

*Primary Examiner*—Sikarl A. Witherspoon
(74) *Attorney, Agent, or Firm*—Steven D. Boyd

(57) ABSTRACT

Process for the manufacture of 1,1-difluoroethane by liquid-phase fluorination of 1,2-dichloroethane using hydrofluoric acid in the presence of a Lewis acid as catalyst and of $FeCl_3$ as cocatalyst. Process for the manufacture of 1,1-difluoroethylene employing it.

18 Claims, No Drawings

METHOD OF PRODUCING 1,1-DIFLUOROETHANE AND APPLICATION THEREOF FOR THE PRODUCTION OF 1,1-DIFLUOROETHYLENE

This application is the national stage of PCT/FR03/03074, filed Oct. 17, 2003, and published as WO 2005/047219 on May 26, 2005.

BACKGROUND OF THE INVENTION

Field of the Invention

A first subject-matter of the present invention is a process for the manufacture of 1,1-difluoroethane by liquid-phase fluorination using hydrofluoric acid (HF) of 1,2-dichloroethane (or D12, of formula $CH_2ClCH_2Cl$) employing a Lewis acid as catalyst. It also relates to a process for the manufacture of 1,1-difluoroethylene comprising a stage consisting of this first process.

1,1-Difluoroethane, of formula $CH_3CHF_2$, is a hydrofluoroalkane or hydrofluorocarbon (HFA or HFC) also known under the name of F152a. It is a substitute for chlorofluorocarbons (CFC) which can be of use in industrial refrigeration but also as expansion agent for foams or as aerosol propellant. It can be used alone or as a mixture. It is known to prepare 1,1-difluoroethane by fluorination of chloroethene (also known as vinyl chloride monomer or VCM) in the liquid phase in the presence of a catalyst. Thus, U.S. Pat. No. 5,714,650 discloses the introduction of VCM in the gaseous state into a reaction medium consisting of a hydrofluoric acid (HF) liquid phase in the presence of a catalyst, such as, in particular, tin tetrachloride ($SnCl_4$). In U.S. Pat. No. 5,672,788, this same reaction is carried out in two stages.

It is also known to prepare 1,1-difluoroethane by reacting 1,1-dichloroethane (also known as D11) with HF in the liquid phase. Japanese Patents JP 50-106904 and JP 50-106905 disclose this reaction in the presence, as catalyst, of $SbCl_5$ and of $SbF_5$ respectively. U.S. Pat. No. 2,452,975 and U.S. Pat. No. 5,672,788 also disclose it in the presence of $SnCl_4$ as catalyst.

However, VCM and D11 have a number of disadvantages as starting material for the preparation of 1,1-difluoroethane, in particular for an industrial manufacture of this compound. Thus, VCM presents industrial health problems related to its toxicity and in particular to its carcinogenic nature. D11 is a starting material which is relatively lacking in availability industrially and is therefore expensive.

1,2-Dichloroethane (also known as D12) offers the advantage of being more readily available for industrial syntheses.

DETAILED DESCRIPTION OF THE INVENTION

However, it is desirable to improve the manufacturing processes, whether as regards yield or alternatively selectivity, particularly for an industrial manufacture which is advantageously carried out continuously.

It has now been found that the use, in the reaction disclosed by U.S. Pat. No. 5,545,775, of a specific cocatalyst in combination with a Lewis acid results in a manufacture of 152a exhibiting a higher yield and a more favourable selectivity.

A subject-matter of the present invention is therefore a process for the manufacture of 1,1-difluoroethane by liquid-phase fluorination of 1,2-dichloroethane using hydrofluoric acid in the presence of a Lewis acid as catalyst, characterized in that the said fluorination is carried out in the presence of $FeCl_3$ as cocatalyst.

It is preferable to use, as catalyst, a Lewis acid comprising a compound based on tin, antimony, titanium, molybdenum, tungsten, niobium or tantalum. Particularly advantageous results can be obtained for compounds based on titanium or tin. A titanium-based compound is very particularly preferred.

The Lewis acids which can be used as catalyst in the process according to the invention are generally halides, such as chloride, fluoride or chlorofluoride. Oxides or oxyhalides can also be used.

When, in accordance with a preferred alternative form of the process according to the invention, a titanium-based Lewis acid is used as catalyst, titanium tetrachloride ($TiCl_4$) has proved to be particularly advantageous.

The reactants and the catalysts which can be used in the process according to the invention are commercially available, as is $FeCl_3$.

The amount of HF (expressed as number of moles) to be used in the process according to the invention is generally at least twice the number of moles of D12 and is preferably much greater. The molar ratio of number of moles of HF divided by the number of moles of D12 can thus be between 2 and 50, preferably between 2 and 20.

The fluorination process according to the invention is carried out in a solvent or mixture of solvents exhibiting an at least partial miscibility with liquid HF and in which the fluorination catalyst is soluble. Suitable solvents can be polar or nonpolar and are preferably fluorinated or chlorofluorinated hydrocarbons.

However, it is preferable to use hydrofluoric acid as solvent, which makes it possible to generally obtain an improved productive output.

The amount of catalyst to be employed can vary within wide limits. It is generally between 0.0005 and 0.5 mol, preferably between 0.001 and 0.1 mol, per mole of solvent present in the reactor. In the case where the solvent is HF, it is preferable to operate with an amount of catalyst in the region of that which can be dissolved in the HF at the reaction temperature.

The amount of $FeCl_3$ cocatalyst necessary can be expressed in the form of cocatalyst/catalyst molar ratio. This ratio is between 0.01 and 1, preferably between 0.05 and 0.5.

The temperature at which the process according to the invention is carried out is generally between 30 and 180° C., preferably between 50 and 130° C.

The pressure used for this same implementation is chosen so as to keep the reaction medium in the liquid phase. It is generally between 0.2 and 5 MPa (2 to 50 bar) absolute, preferably between 0.5 and 4 MPa (5 to 40 bar) absolute.

The necessary reaction time, which depends on the amount of reactants charged at the start and on the various operating parameters, can be easily known experimentally. It can vary from approximately 1 hour to 20 hours, preferably from 1 to 10 hours, in the case of a batchwise or semicontinuous process. In the case of a continuous process, the residence time, defined as the ratio of the volume of the reaction medium to the flow rate by volume of the reactants, is advantageously between 1 and 20 hours, preferably between 1 and 10 hours.

The liquid-phase fluorination process according to the invention can be carried out semicontinuously or continuously.

When the said process is carried out semicontinuously, the reaction is carried out in equipment composed of an autoclave surmounted by a simple condenser, or by a retrogradation column with a reflux condenser at the top, and by a pressure-regulating valve. The reactants, the catalyst and the solvent are introduced into the autoclave before the beginning of the reaction. The reaction products with low boiling points (F152a, HCl and possibly VCM, which is a reaction intermediate) are extracted continuously during the reaction. The heavy compounds with higher boiling points (D12, HF and 1-chloro-1-fluoroethane or F151a formed as an intermediate) are largely refluxed in the liquid form into the reaction medium by virtue of the condenser (or retrogradation column) placed above the autoclave. The F152a is subsequently isolated, for example by distillation, from the crude reaction mixture or from the final reaction products.

When, according to a preferred alternative form, the process is carried out continuously, use is also made of equipment composed of an autoclave surmounted by a simple condenser, or by a retrogradation column with a reflux condenser at the top, and by a pressure-regulating valve. If the operation is carried out in a solvent other than HF, one of the two reactants (or both) is (or are) introduced continuously into the reaction medium comprising the catalyst and the solvent, it also being possible for the other to be introduced into the autoclave before the beginning of the reaction. If the operation is carried out with HF as solvent, part of the latter is introduced with the catalyst into the autoclave before the beginning of the reaction, and D12 and HF are introduced continuously into the reaction medium. The reaction products are extracted continuously during the reaction and the reactants are largely refluxed in the liquid form into the reaction medium. The F152a is subsequently isolated, for example by distillation, from the crude reaction mixture or from the final reaction products.

In the case of a continuous industrial process, it may be preferable to introduce D12 and HF continuously into the initial charge, composed mainly of hydrofluoric acid, the catalyst and the cocatalyst as defined above. In this case, the HF/D12 molar ratio corresponding to the amount of these compounds introduced is generally between 2 and 5 and preferably equal to approximately 2.

In this continuous embodiment, small amounts of F151a, D12 and HF can accompany the products formed. The gas mixture thus obtained then requires various separation stages known to a person skilled in the art (such as a distillation, an extraction or a separation by settling) in order to obtain pure F152a and to recycle the D12, the F151a and the HF to the reactor.

Furthermore, in the semicontinuous and continuous embodiments, the fluorination is advantageously carried out at a pressure corresponding to the reflux of the reaction medium at the desired temperature. The temperature of the condenser is advantageously set at a value from −50 to 150° C., preferably from −20 to 50° C.

Whatever the embodiment of the process according to the invention, the material used for the reactor is generally chosen from those which are resistant to the corrosion brought about by superacid media comprising HF. Use may thus be made of stainless steel or various alloys known to a person skilled in the art, such as:

- an alloy composed essentially of at least 70% Ni, 14 to 18% Cr, from 6 to 10% Fe and having a Cu content of less than 1%, generally known under the name of Inconel®; or else
- an alloy of Monel® or Hastelloy® type.

Another subject-matter of the present invention is a process for the manufacture of 1,1-difluoroethylene (also known as VF2) comprising:

(i) the preparation of 1,1-difluoroethane from 1,2-dichloroethane according to the process defined above, then
(ii) the gas-phase chlorination of the 1,1-difluoroethane thus obtained to 1-chloro-1,1-difluoroethane (also known as F142b) at a temperature of between 30 and 150° C., preferably between 50 and 120° C., then
(iii) the gas-phase pyrolysis of the 1-chloro-1,1-difluoroethane thus obtained at a temperature of between 500 and 600° C., preferably between 520 and 580° C., and in the absence of catalyst.

The following examples are given purely by way of illustration of the present invention and should not be interpreted as limiting the scope thereof.

EXAMPLE 1

Semicontinuous Synthesis of F152a from D12 with $TiCl_4$ as Catalyst and $FeCl_3$ as Cocatalyst The equipment used is composed of a stirred autoclave with a capacity of 0.1 litre, made of stainless steel 316L, surmounted by a simple condenser and by a pressure-regulating valve. This autoclave is immersed in liquid nitrogen and the following are successively introduced: 2.5 mol of HF, 0.25 mol of D12, 0.02 mol of $TiCl_4$ and 0.0025 mol of $FeCl_3$. The temperature of the autoclave is then brought back to ambient temperature. The autoclave is then immersed in an oil bath, the temperature of which is brought to 140° C. while the temperature of the condenser is maintained at approximately 17° C. The regulating pressure is set at 2.0 MPa (20 bar) absolute. At this pressure, the temperature of the medium is on average in the region of approximately 120° C. During the reaction, the volatile reaction products are continuously discharged, passing into a water-filled wash bottle with a capacity of 1l and then into a dryer, before being collected in a stainless steel trap cooled with liquid nitrogen. After reacting for 1.5 hours, the autoclave is cooled. After returning to ambient temperature, the autoclave is degassed and the reaction products are washed, dried and trapped as above. The gas phase and the liquid phase of the various traps are analysed, as is the liquid phase possibly remaining in the autoclave after the degassing.

The F152a yield, expressed as being the ratio of the number of moles of F152a detected to the number of moles of D12 initially charged, is 46%.

EXAMPLE 2

Comparative: Semicontinuous Synthesis of F152a from D12 with $TiCl_4$ as Catalyst and in the Absence of $FeCl_3$.

The equipment used is exactly that described in Example 1. This autoclave is immersed in liquid nitrogen and the following are introduced: 2.5 mol of HF, 0.25 mol of D12 and 0.02 mol of $TiCl_4$. The temperature of the autoclave is then brought back to ambient temperature. The autoclave is then immersed in an oil bath, the temperature of which is brought to 140° C. while the temperature of the condenser is maintained at 20° C. The regulating pressure is set at 2.0 MPa (10 bar) absolute. At this pressure, the temperature of the medium is on average in the region of approximately 120° C. The procedure is exactly the same as that described in Example 1 but the reaction time is on this occasion 3.5 hours.

The F152a yield is 21%.

It is thus apparent that the presence of $FeCl_3$ in Example 1, as cocatalyst, makes it possible to more than double the F152a yield.

EXAMPLE 3

Semicontinuous Synthesis of F152a from D12 with $TiCl_4$ as Catalyst and $FeCl_3$ as Cocatalyst The equipment used is on this occasion composed of an autoclave similar to that of Example 1 but with a capacity of 1 litre.

This autoclave is immersed in liquid nitrogen and the following are successively introduced: 10 mol of HF, 0.5 mol of D12, 0.04 mol of $TiCl_4$ and 0.008 mol of $FeCl_3$. The temperature of the autoclave is then brought back to ambient temperature. The autoclave is then immersed in an oil bath, the temperature of which is brought to 140° C. while the temperature of the condenser is maintained at approximately 90° C. The regulating pressure is set at 1.0 MPa (10 bar) absolute. At this pressure, the temperature of the medium is on average in the vicinity of approximately 95-100° C. The reaction time is 3 hours. The procedure during the reaction and after the reaction is similar to that of Example 1.

The conversion of the D12 was calculated by taking the ratio of the number of moles of D12 consumed (number of starting moles of D12 minus the number of moles of D12 after reaction) to the number of starting moles of D12. The selectivity for F152a was calculated by taking the ratio of the number of moles of F152a obtained to the number of moles of D12 consumed.

A degree of conversion of the D12 of 87% for a degree of selectivity for F152a of 90%, corresponding to an overall yield of 78%, is thus obtained.

EXAMPLE 4

Continuous Synthesis of F152a from D12 with $TiCl_4$ as Catalyst and $FeCl_3$ as Cocatalyst The equipment used is composed of a stirred autoclave with a capacity of 1 litre, made of stainless steel 316L, which makes possible the continuous introduction of the reactants D12 and HF. This autoclave is surmounted by a simple condenser and by a pressure-regulating valve. This autoclave is immersed in liquid nitrogen and a charge of 500 g of HF (25 mol), 38 g of $TiCl_4$ (0.2 mol) and 2.5 g of $FeCl_3$ (0.015 mol) is introduced. The temperature of the autoclave is then brought back to ambient temperature. The autoclave is then immersed in an oil bath, the temperature of which is brought to 140° C. while the temperature of the condenser is maintained at 15° C. The regulating pressure is set at 1.0 MPa (10 bar) absolute. At this pressure, the temperature of the medium is on average in the vicinity of approximately 95° C.

When the temperature of the medium is reached, D12 is introduced continuously into the reaction medium using a pump, via a dip pipe in the liquid phase, with a flow rate of approximately 0.25 mol/h and HF is introduced via a regulating flowmeter with a flow rate of approximately 0.5 mol/h. During the reaction, the volatile reaction products are continuously discharged, passing into a water-filled wash bottle with a capacity of 1 l and then into a dryer, before being collected in a stainless steel trap cooled with liquid nitrogen.

After reacting for 30 h (corresponding to 8.6 mol of D12 fed in), the autoclave is cooled by circulation of water. After returning to ambient temperature, the autoclave is degassed and the reaction products are washed, dried and trapped as above. The gas phase and the liquid phase of the various traps are analysed, as is the liquid phase possibly remaining in the autoclave after the degassing.

The F152a content in the volatile reaction products discharged during the test is 98% (in moles) and a degree of conversion of the D12 of 80% is measured.

The presence is observed in the autoclave of solid heavy residual organic by-products, the amount of which is measured after extraction of the catalyst and of the cocatalyst. The amount of these by-products, formed at the expense of the desired F152a, amounts to 6 g, i.e. 0.7% by weight with respect to the amount of D12 introduced during the test.

EXAMPLE 5

Comparative: Continuous Synthesis of F152a from D12 with $TiCl_4$ as Catalyst in the Absence of $FeCl_3$ as Cocatalyst The equipment used is similar to that of Example 4. This autoclave is immersed in liquid nitrogen and a charge of 500 g of HF (25 mol) and 38 g of $TiCl_4$ (0.2 mol) is introduced. The temperature of the autoclave is then brought back to ambient temperature. The autoclave is then immersed in an oil bath, the temperature of which is brought to 140° C. while the temperature of the condenser is maintained at 15° C. The regulating pressure is set at 1.0 MPa (10 bar) absolute. At this pressure, the temperature of the medium is on average in the vicinity of approximately 95° C.

As above, the D12 flow rate is approximately 0.25 mol/h and the HF flow rate is approximately 0.5 mol/h. The procedure during and after the reaction is exactly alike.

After reacting for 29 h (corresponding to 7.3 mol of D12 fed in), the autoclave is cooled by circulation of water.

The F152a content in the volatile reaction products discharged during the test is 98% (in moles) and a degree of conversion of the D12 of 75% is measured.

The presence is also observed in the autoclave of residual organic by-products, the amount of which is 24 g, i.e. 3.3% by weight with respect to the amount of D12 introduced during the test.

This amount of by-products is very markedly greater than that of Example 4 (by a factor of approximately 5).

The result of this is that the said Example 4 exhibits, as a result of the $FeCl_3$ cocatalyst, a markedly improved selectivity for F152a, which is highly advantageous for a continuous industrial manufacturing process.

The invention claimed is:

1. Process for the manufacture of 1,1-difluoroethane by liquid-phase fluorination of 1,2-dichloroethane using hydrofluoric acid in the presence of a Lewis acid as catalyst, characterized in that the said fluorination is carried out in the presence of $FeCl_3$ as cocatalyst.

2. Process according to claim 1, characterized in that use is made of a Lewis acid comprising a compound based on tin, antimony, titanium, molybdenum, tungsten, niobium or tantalum.

3. Process according to claim 1, characterized in that the Lewis acid is a titanium-based compound.

4. Process according to claim 1, characterized in that the Lewis acid is a halide, an oxide or an oxyhalide.

5. Process according to claim 1, characterized in that the Lewis acid is titanium tetrachloride.

6. Process according to claim 1, characterized in that it is carried out in hydrofluoric acid as solvent.

7. Process according to claim 6, characterized in that the amount of catalyst to be employed is between 0.0005 and 0.5 mol, preferably between 0.001 and 0.1 mol, per mole of solvent.

8. Process according to claim 1, characterized in that the cocatalyst/catalyst molar ratio is between 0.01 and 1, preferably between 0.05 and 0.5.

9. Process according to claim 1, characterized in that its implementation temperature is between 30 and 180° C.

10. Process according to claim 1, characterized in that its implementation pressure is between 0.2 and 5 MPa absolute.

11. Process according to claim 1, characterized in that it is carried out continuously.

12. Process for the manufacture of 1,1-difluoroethylene comprising:
  (i) the preparation of 1,1-difluoroethane from 1,2-dichloroethane according to the process defined in, then
  (ii) the gas-phase chlorination of the 1,1-difluoroethane thus obtained to 1-chloro-1,1-difluoroethane at a temperature of between 30 and 150° C., then
  (iii) the gas-phase pyrolysis of the 1-chloro-1,1-difluoroethane thus obtained at a temperature of between 500 and 600° C., and in the absence of catalyst.

13. Process according to claim 6, characterized in that the amount of catalyst to be employed is between 0.001 and 0.1 mol per mole of solvent.

14. Process according to claim 1, characterized in that the cocatalyst/catalyst molar ration is between 0.05 and 0.5.

15. Process according to claim 1, characterized in that its implementation temperature is between 50 and 130° C.

16. Process according to claim 1, characterized in that its implementation pressure is between 0.5 and 4 MPa absolute.

17. Process according to claim 12, characterized in that said gas-phase chlorination temperature is between 50 and 120° C.

18. Process according to claim 12, characterized in that said gas-phase pyrolysis temperature is between 520 and 580° C.

* * * * *